(12) United States Patent
Chang et al.

(10) Patent No.: US 7,498,045 B2
(45) Date of Patent: Mar. 3, 2009

(54) BIODEGRADABLE POLYMERIC NANOCAPSULES AND USES THEREOF

(75) Inventors: Thomas M. S. Chang, 165 Du Bearn, St-Lambert, Québec (CA) J4S 1K9; Wei-Ping Yu, Clarksville, MD (US); Douglas Powanda, Brossard (CA)

(73) Assignee: Thomas M. S. Chang

( * ) Notice: Subject to any disclaimer, the term of this patent is extended or adjusted under 35 U.S.C. 154(b) by 56 days.

(21) Appl. No.: 10/488,116

(22) PCT Filed: Aug. 28, 2002

(86) PCT No.: PCT/CA02/01331

§ 371 (c)(1),
(2), (4) Date: Dec. 12, 2004

(87) PCT Pub. No.: WO03/017987

PCT Pub. Date: Mar. 6, 2003

(65) Prior Publication Data

US 2005/0123617 A1    Jun. 9, 2005

(51) Int. Cl.
*A61K 9/16* (2006.01)

(52) U.S. Cl. .................. 424/490; 424/450; 424/489; 424/491

(58) Field of Classification Search ............... 424/490, 424/522, 529, 491, 489, 450, 501; 435/177
See application file for complete search history.

(56) References Cited

U.S. PATENT DOCUMENTS

| | | | | |
|---|---|---|---|---|
| 4,001,401 A | * | 1/1977 | Bonsen et al. ............ | 514/6 |
| 5,573,934 A | * | 11/1996 | Hubbell et al. ........... | 435/177 |
| 5,578,325 A | * | 11/1996 | Domb et al. .............. | 424/501 |
| 5,683,723 A | * | 11/1997 | Spenlehauer et al. ..... | 424/501 |
| 6,294,204 B1 | * | 9/2001 | Rossling et al. .......... | 424/497 |
| 6,887,974 B2 | * | 5/2005 | Pathak .................... | 530/200 |
| 2003/0087985 A1 | * | 5/2003 | Hubbell et al. ........... | 523/114 |

OTHER PUBLICATIONS

Chang et al. Advanced Drug Delivery Reviews 40 (2000) 213-218.*

* cited by examiner

*Primary Examiner*—Michael G. Hartley
*Assistant Examiner*—James Rogers
(74) *Attorney, Agent, or Firm*—Klauber & Jackson, LLC

(57) ABSTRACT

The present invention relates to a biodegradable polymeric nanocapsule composition, adaptable for encapsulation of an agent of therapeutic interest for enhancing the in vivo circulation time of thereof and uses thereof.

64 Claims, 6 Drawing Sheets

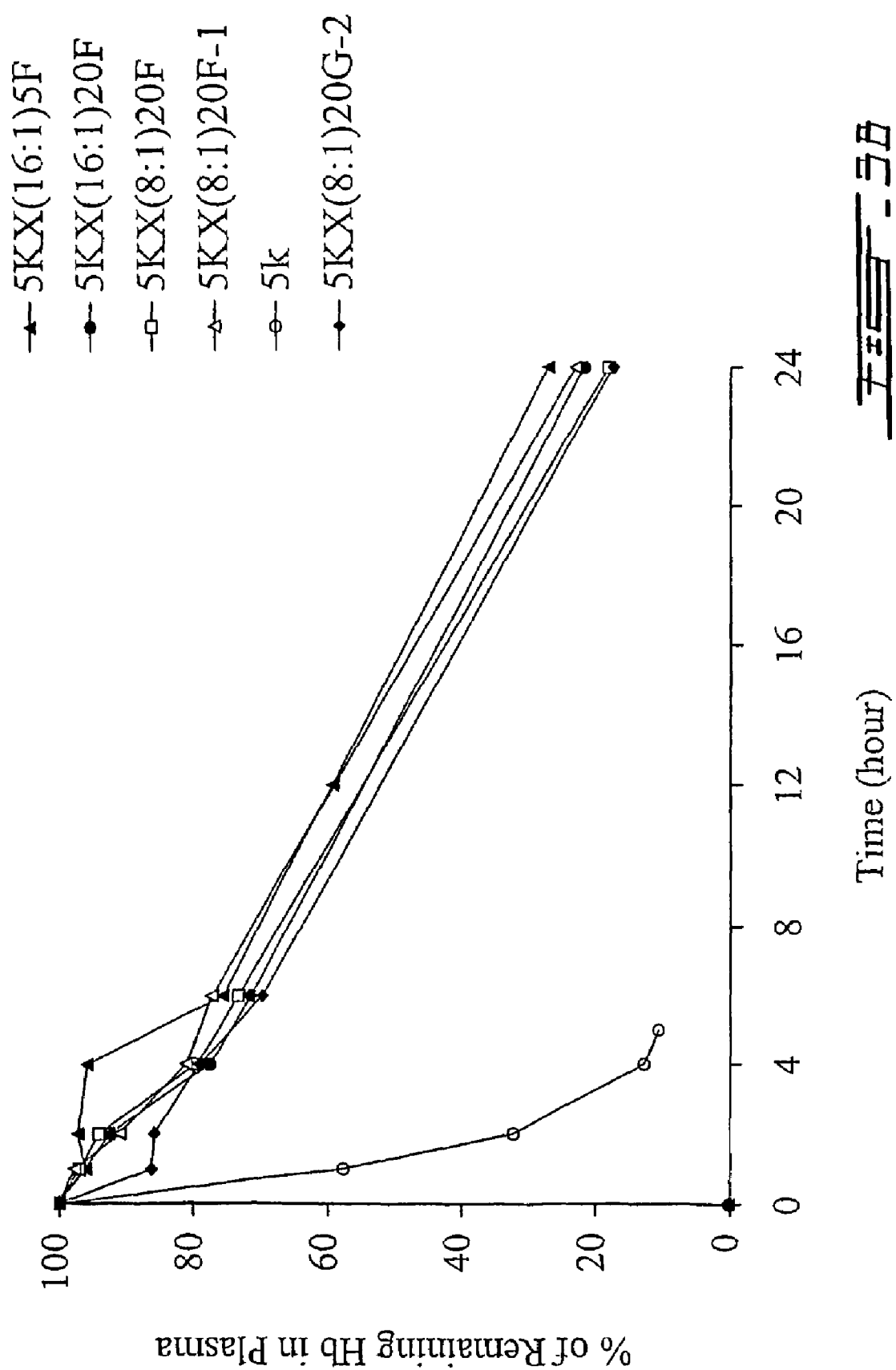

BIODEGRADABLE POLYMERIC NANOCAPSULES AND USES THEREOF

BACKGROUND OF THE INVENTION (a) Field of the Invention

The invention relates to the field of nanocapsule compositions having improved circulation times, uses thereof, and methods for preparing the same. The nanocapsule compositions of the present invention are adaptable to encapsulate agents of therapeutic interest, including macromolecules.

(b) Description of Prior Art

Hemoglobin (Hb) in red blood cells (RBC) is responsible for transporting oxygen. When extracted from a RBC, Hb can be sterilized to remove H.I.V. and other infective agents. Unfortunately, when the extracted Hb is infused into the body, it breaks down into dimers after infusion into the circulation of a recipient. Free Hb is also toxic especially for the kidney. Hemoglobin molecules can be chemically modified to prevent degradation after infusion. These simple modified hemoglobins are in the final stages of human testing. However, this type of modified hemoglobin is not covered by a membrane and as a result, it has to be ultra-pure to avoid adverse reactions. This also removes all the red blood cell enzymes that are needed to prevent the damaging effects of oxidants. Furthermore, the circulation half-time of modified hemoglobin in human is rather short, at approximately 24 hours.

Hemoglobin is but one example of the many biologically important macromolecules required by the body. In the event of illness, it is often desirable to supplement the body with macromolecules that are either lacking as a result of the illness or identified to have a therapeutic effect. Unfortunately, however, it has been difficult in the past to adequately deliver such macromolecules into the body in an acceptable manner to obtain the desired therapeutic effect.

In the past, attempts to microencapsulate hemoglobin for in vivo use have been made (Chang, T. M. S., 1964, *Science* 146, 524; Chang, T. M. S., 1997, "*Blood Substitutes:Principles, methods, products and clinical trial*", vol. I, Karser publisher, Basel). Collodion, cellulose, HMDA (1,6-hexamethylenediamine), cross-linked protein, bilayer of phospholipid-cholesterol complexed on cross-linked protein membrane and other materials have been used to coat droplets of hemoglobin solution (Chang, T. M. S., 1997, "*Blood Substitutes:Principles, methods, products and clinical trial*", vol. I, Karser publisher, Basel). However, these artificial cells with diameters of about one micron survived for a very short time in the host circulation following intravenous injections. Furthermore, the polymer membrane of these artificial cells accumulated in the body.

Emphasis then turned to the use of phospholipids in the preparation of liposomes containing hemoglobin (Chang, T. M. S., 1997, "*Blood Substitutes:Principles, methods, products and clinical trial*", vol. I, Karser publisher, Basel). The use of submicron phospholipid-cholesterol microcapsules (liposomes) increased the survival time of hemoglobin in the circulation (Djordjevich, L. et al., 1980, *Exp. Hematol.* 8, 584). The drawback to these liposomes is their insufficient stability and strength and also the sensitivity of the phospholipid membranes to environmental degradation. Liposomes are subject to degradation during storage and while in host circulation. Furthermore, the lipid membranes are removed and accumulated in cells that are normally needed to remove bacteria and toxin from the circulation. As a result, the body's ability to fight infection and toxin can be markedly reduced.

Subsequently, a biodegradable polymer membrane containing hemoglobin was developed, as described in Applicant's U.S. Pat. No. 5,670,173, which is herein incorporated by reference. Here, a biodegradable polylactide membrane containing hemoglobin of about 150 nanometre diameter was prepared (T. M. S. Chang and W. P. Yu, U.S. Pat. No. 5,670,173 issued on Sep. 23, 1997). Polylactide can be readily converted to water and carbon dioxide after use and therefore does not accumulate in the body.

On average, after infusion, the polymer membrane as disclosed in U.S. Pat. No. 5,670,173 circulates with a half-time of less than 2 hours. It has been subsequently determined that for practical purposes, such as blood substitutes, for example, a biodegradable polymer membrane having a longer circulation half-time is preferred.

Accordingly, it would be highly desirable to be provided with a multi-purpose biodegradable nanocapsule having an improved in vivo circulation time.

It would also be highly desirable to be provided with a biodegradable nanocapsule having an effective circulation time of at least 6 hours.

It would be further desirable to be provided with a biodegradable nanocapsule having an effective circulation time of at least 14 hours.

It would be further desirable to be provided with a biodegradable nanocapsule having an effective circulation time of at least 24 hours.

It would be yet further desirable to be provided with a multi-purpose biodegradable nanocapsule that is selectively permeable to therapeutic agents of interest.

It would also be desirable to be provided with a multi-purpose biodegradable nanocapsule that is adaptable for the encapsulation of an agent of therapeutic interest, and delivery thereof in vivo.

It would be further desired to be provided with a nanocapsule composition adaptable to deliver an encapsulated agent of therapeutic interest in vivo with a controlled rate of release.

SUMMARY OF THE INVENTION

The present invention provides a multi-purpose biodegradable nanocapsule having an improved in vivo circulation time. The biodegradable nanocapsules of the present invention are adaptable for encapsulating an agent of therapeutic interest and subsequently delivering the same in vivo. The biodegradable nanocapsules of the present invention may be employed to encapsulate a plurality of agents of therapeutic interest, including, without limitation, macromolecules, such as hemoglobin, enzymes, polypeptides, genes, and polymerized proteins and enzymes such as polyhemoglobin etc.

Preferably, the biodegradable nanocapsules of the present invention are adaptable for the controlled release of a variety of encapsulated therapeutic agents, including macromolecules, into in vivo circulation of a recipient upon administration thereto. The nanocapsule compositions of the present invention are further adapted to encapsulate therapeutically effective concentrations of an agent of therapeutic interest and deliver the same into in vivo circulation of a recipient.

In addition, the nanocapsules of the present invention are adaptable to provide controlled release of an encapsulated agent of therapeutic interest in vivo.

According to one embodiment of the present invention a method for preparing a biodegradable nanocapsule having a circulation half-time of at least 35 hours in vivo is provided. This nanocapsule has been shown to effectively deliver an exemplary macromolecule of interest into in vivo circulation with a controlled release rate providing a circulation half-time of the macromolecule of at least 14 hours.

A number of novel approaches were employed in accordance with the present invention to adapt the nanocapsule compositions to release encapsulated macromolecules at controlled rates in vivo. For example, a nanocapsule composition of the present invention was adapted to alter the release rate of encapsulated proteins from a half time of 2 hours in step-wise fashion to a release rate of a half time of at least 24 hours. Accordingly, the present invention provides a nanocapsule composition having an improved circulation time that can maintain an encapsulated agent of therapeutic interest in in vivo circulation for a prolonged period of time. As such, the nanocapsule of the present invention provides a versatile carrier for in vivo delivery and controlled release of a plurality of agents of therapeutic interest encapsulated therein.

One aim of the present invention is to provide a multipurpose biodegradable nanocapsule having an improved in vivo circulation time.

Another aim of the present invention is to provide a biodegradable nanocapsule membrane having an effective circulation half-time of at least 35 hours.

Another aim of the present invention is to provide a biodegradable nanocapsule composition having an effective circulation half-time of at least 6 hours.

Another aim of the present invention is to provide a biodegradable nanocapsule composition having an effective circulation half-time of at least 14 hours.

Yet another aim of the present invention is to provide a biodegradable nanocapsule composition having an effective circulation half-time of at least 24 hours.

Another aim of the present invention is to provide a multipurpose biodegradable nanocapsule that is selectively permeable to biological agents of therapeutic interest.

Another aim of the present invention is to provide a multipurpose biodegradable nanocapsule composition adaptable for the controlled release or delivery of a variety of therapeutic agents of interest in vivo.

A further aim of the present invention is to provide a method for preparing a nanocapsule composition having an improved circulation time in vivo.

Yet a further aim of the present invention is to provide a method for delivering an agent of therapeutic interest in vivo.

In accordance with the present invention there is provided a biodegradable polymeric nanocapsule membrane composition adaptable for encapsulating an agent of therapeutic interest and enhancing in vivo circulation time thereof, said nanocapsule membrane composition comprising a copolymer of polylactic acid polymer and polyethylene glycol wherein said copolymer is soluble in acetone and insoluble in water.

In accordance with another aspect of the present invention there is provided a hemoglobin nanocapsule composition, said composition comprising a biodegradable polymeric nanocapsule membrane encapsulating a therapeutically effective concentration of a hemoglobin preparation; said nanocapsule membrane comprising a copolymer of polylactic acid polymer and polyethylene glycol; said copolymer being soluble in acetone and insoluble in water; wherein said nanocapsule composition is adaptable for enhancing the in vivo circulation time of said hemoglobin preparation.

The hemoglobin nanocapsule composition of the present invention may include other biological agents known to inhibit the production of methemoglobin. Furthermore, the hemoglobin nanocapsule composition of the present invention may be adapted to be selectively permeable to molecules present in in vivo circulation, that prevent the hemoglobin in the nanocapsules from becoming methemoglobin.

In accordance with another aspect of the present invention there is further provided a method for preparing a nanocapsule composition having an enhanced circulation time in vivo, said method comprising: (a) preparing a copolymer mixture of a polylactic acid polymer and polyethylene glycol (PLA-PEG); (b) heating said copolymer mixture; (c) adding an aqueous solution comprising an agent of therapeutic interest to said copolymer mixture; (d) precipitating said copolymer mixture from said aqueous solution; and (e) extracting the nanocapsule composition therefrom; wherein said composition comprises a biodegradable, polymeric nanocapsule membrane encapsulating said agent of therapeutic interest.

The method of the present invention for preparing a nanocapsule composition having enhanced circulation time in vivo, may further include incubating the agent of therapeutic interest with a cross-linker component prior to mixing the agent together with the PLA-PEG preparation. Alternatively, or in addition, the method for preparing a nanocapsule composition of the present invention may further include cross-linking at least some of the encapsulated agent of therapeutic interest to an internal surface of the nanocapsule, wherein a cross-linker component is added subsequent to the mixing of the PLA-PEG mixture with the agent of therapeutic interest.

A cross-linker component of the present invention may be glutaraldehyde. However, it is fully contemplated that alternatives to this cross-linker component, as known in the art, may be employed.

In accordance with still a further aspect of the present invention there is further still provided a delivery system for enhancing the circulation time of an agent of therapeutic interest in vivo, said system comprising: a biodegradable polymeric nanocapsule composition comprising of a copolymer membrane encapsulating said agent of therapeutic interest; wherein said copolymer membrane includes a copolymer of polylactic acid and polyethylene glycol and is soluble in acetone and insoluble in water; said copolymer membrane being adaptable to deliver the encapsulated agent of therapeutic interest into in vivo circulation at a controlled rate of release.

In accordance with the present invention there is still further provided a delivery system for providing the step-wise release of an agent of therapeutic interest in vivo, said system comprising: a plurality of biodegradable polymeric nanocapsule compositions each adapted to release an encapsulated agent of therapeutic interest at a different predetermined rate of release in vivo; wherein each of said plurality of biodegradable polymeric nanocapsules includes a copolymer membrane comprising a copolymer of polylactic acid and polyethylene glycol, said copolymer being soluble in acetone and insoluble in water.

Furthermore, the drug delivery system of the present invention may be further adapted to be selectively permeable to biological components present in in vivo circulation of the recipient. According to this embodiment of the present invention, the quality and integrity of the encapsulated agent of therapeutic interest may be maintained.

Alternatively, or in addition to, the drug delivery system of the present invention may also be adapted to encapsulate other biological components together with the agent of therapeutic interest. According to an alternative embodiment of the present invention, a drug delivery system having improved in vivo stability is provided whereby at least a portion of the encapsulated drug or agent of therapeutic interest is cross-linked to the internal surface of the nanocapsule.

In accordance with the present invention there is also provided a nanocapsule composition comprising a biodegradable polymeric nanocapsule membrane encapsulating a therapeutically effective concentration of a macromolecule; said nanocapsule membrane comprising a copolymer of polylactic acid polymer and polyethylene glycol; said copolymer being soluble in acetone and insoluble in water; wherein said nanocapsule composition is adaptable for enhancing the in vivo circulation time of said macromolecule.

For the purpose of the present invention the following terms are defined below.

The term "therapeutic agent" is intended to mean any agent having a therapeutic potential when administered in vivo, including, without limitation, macromolecules such as hemoglobin, proteins, enzymes, RNA, DNA, and genes.

BRIEF DESCRIPTION OF THE DRAWINGS

FIGS. 3A and 3B illustrate the circulation time of a variety of nanocapsule compositions in accordance with the present invention;

DETAILED DESCRIPTION OF THE INVENTION

Figure 1:
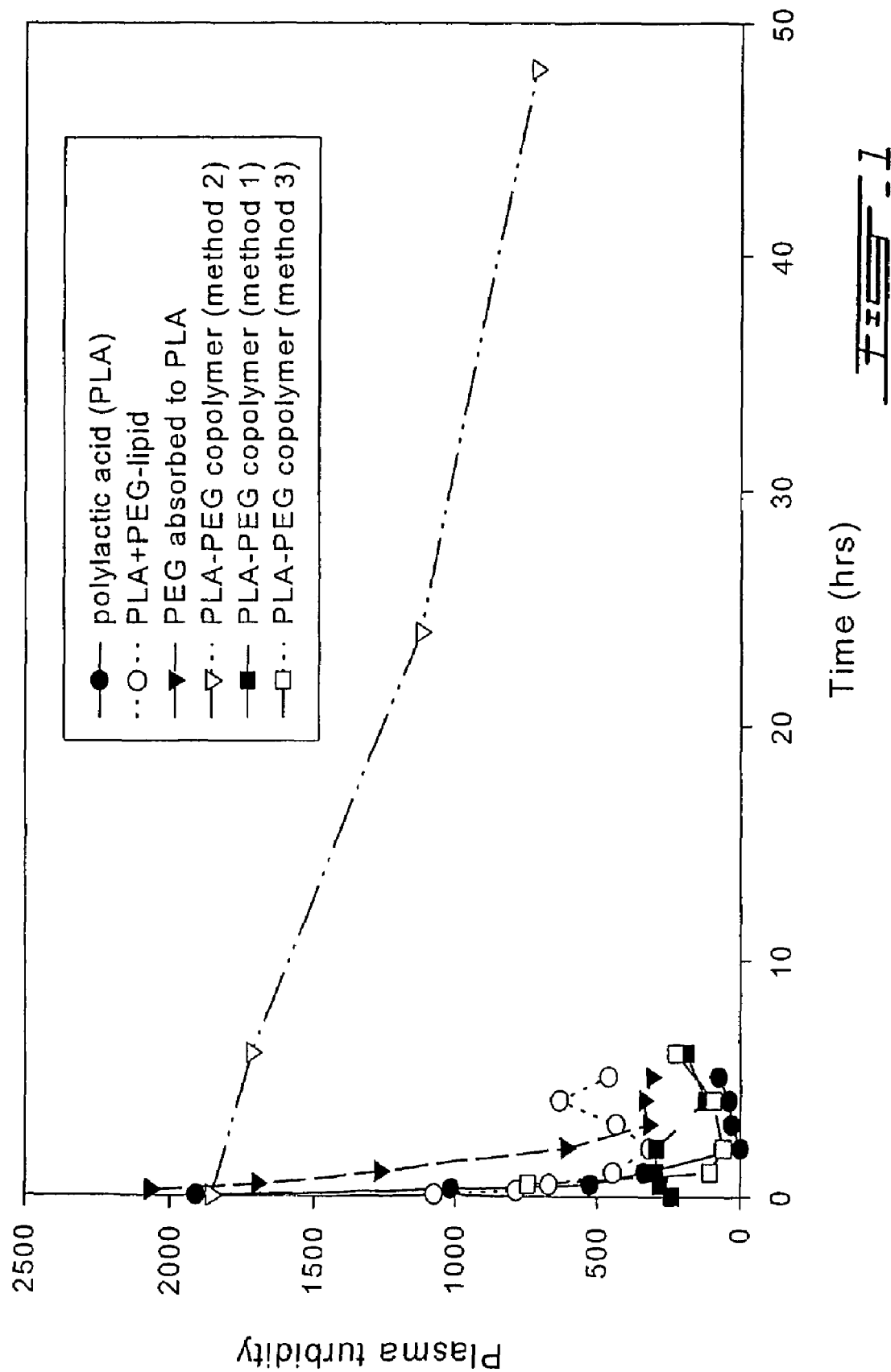
FIG. 1 illustrates a graphical representation of the circulation times of a variety of nanocapsule compositions in accordance with the present invention.

In accordance with the present invention, improved biodegradable nanocapsules having an increased in vivo circulation time are provided. Preferably, the biodegradable nanocapsules of the present invention are polymeric nanocapsules. The biodegradable nanocapsules of the present invention are adaptable to encapsulate agents of therapeutic interest and deliver the same into in vivo circulation upon administration to a recipient. Furthermore, the nanocapsule compositions of the present invention are adaptable for prolonging the in vivo circulation time of the encapsulated agent contained therein. For practical therapeutic applications, such as blood substitutes, a nanocapsule composition having an in vivo circulation half-time of at least 14 hours, is preferred. As a result, extensive research and development was carried out in connection with the present invention to devise a nanocapsule composition having an increased circulation time in vivo. A novel approach is herein demonstrated, without limitation, in connection with hemoglobin to provide a hemoglobin nanocapsule composition having an improved circulation time and/or controlled rate of release, in vivo.

The present invention provides a novel nanocapsule composition adaptable to encapsulate and effectively deliver agents of therapeutic interest. For example, together with hemoglobin, the nanocapsule composition may be employed to provide a blood substitute. By increasing the in vivo circulation time of an encapsulated agent, a nanocapsule composition of the present invention can significantly increase the duration of functioning of the encapsulated agent in vivo, thereby enhancing the therapeutic effect of the composition. In addition, the nanocapsule composition of the present invention can effectively deliver a given dosage of a therapeutic agent in a controlled manner, thus improving the effectiveness of the dosage while reducing the overall administration required.

According to a preferred aspect of the present invention, a therapeutically effective amount of hemoglobin is encapsulated in a nanocapsule composition and adapted for delivery into the in vivo circulation of a recipient, administered therewith. The encapsulated hemoglobin carries out its function as a blood substitute in transporting oxygen in vivo. Furthermore, when the encapsulated hemoglobin is released from the nanocapsule membrane, it continues to function in the transport of oxygen, thus serving to enhance the total length of function of ht encapsulated hemoglobin in vivo.

The present invention further provides a novel delivery system for the controlled release of a therapeutic agent into in vivo circulation. The ability to modify or adapt the nanocapsule compositions of the present invention to provide a controlled rate of release of the encapsulated agent serves to further provide a novel therapeutic delivery system. Furthermore, a variety of nanocapsule compositions of the present invention may be employed together to provide an effective step-wise therapeutic delivery system. According to this aspect of the present invention, each nanocapsule composition is adapted to deliver an encapsulated agent of therapeutic interest at a predetermined rate of release. When a plurality of these nanocapsule compositions, each having a predetermined rate of release, are administered simultaneously, the encapsulated agent of therapeutic interest is released in vivo in a step-wise fashion.

According to one embodiment of the present invention biodegradable polymeric nanocapsules are provided having an in vivo circulation half time of at least 35 hours, as discussed below. The nanocapsule compositions of the presents invention are adapted to encapsulate a variety of different therapeutic agents, including macromolecules such as hemoglobin, enzymes, RNA, DNA, and other proteins including very large polymerized hemoglobin and enzymes and deliver the same in vivo at a controlled rate of release thereby improving the in vivo circulation time of the encapsulated agent. The nanocapsules compositions of the present invention are further adapted to serve as carriers for therapeutically effective concentrations of an agent of therapeutic interest, providing the controlled in vivo release thereof. According to the present invention, an agent of therapeutic interest may be, without limitation, a macromolecule.

According to one embodiment of the present invention, while the nanocapsules maintain their circulation half-time of 35 hours, we were able to vary the release rate of the enclosed proteins from a release rate of a half time of 2 hours in step-wise fashion to a release rate of a half-time of at least 24 hours in rats. As discussed further hereinbelow, it is expected that the in vivo circulation half-time of the nanocapsule compositions of the present invention would be even greater in humans. Thus, according to the present invention a versatile delivery system for the controlled in vivo release of a variety of therapeutic agents is provided.

An agent of therapeutic interest, for example, may be encapsulated by a nanocapsule composition of the present invention and introduced into in vivo circulation of a recipient by any one of a variety of methods of nanocapsule delivery. For example, a nanocapsule composition of the present invention may be administered by, without limitation, intravenous, intramuscular, intraperitoneal, or subcutaneous delivery, orally or by topical administration. The nanocapsule composition can be modified to provide a controlled rate of release of the encapsulated agent from the nanocapsule carrier. As a result, the agent of interest may be introduced into in vivo circulation at a controlled rate of release for achieving a desired therapeutic effect. The rate of release of a nanocapsule composition of the present invention can be adapted to achieve a desired rate of release of an encapsulated agent of therapeutic interest in a variety of ways, as exemplified herein below.

As exemplified in accordance with the present invention, it is possible to encapsulate hemoglobin within a nanocapsule carrier to obtain a therapeutically effective circulation time thereof, in vivo. Thus, it is fully contemplated that the nanocapsule composition of the present invention is adaptable to encapsulate virtually any agent of therapeutic interest including macromolecules, in a therapeutically effective concentration, for the purpose of providing a controlled drug delivery system.

In accordance with the present invention, a method for the preparation of an nanocapsule composition may include, without limitation, altering the permeability of a nanocapsule membrane; decreasing the rate of degradability of the nanocapsule membrane; or increasing the molecular size of the enclosed agent of therapeutic interest to adapted the nanocapsule composition to maintain a desired circulation half-time and/or controlled rate of release of the encapsulated agent of therapeutic interest is provided.

Materials & Methods

Materials

Polylactic Acid

Polylactic acid (PLA) is obtained from Polysciences Inc. (Canada). Isobutyl 2-cyanoacrylate (IBCA), surfactants (Tween 20™, Span 85™, Triton X 100™, and Pluronic F68™), ethyl cellulose and L-α-Phosphatidylcholine (hydrogenated) and other phospholipids, such as distearoyl phosphatidylcholine (DSPC) or DSPG and tocopherol acetate were obtained from Sigma Chemical Co. (U.S.A.). Dialysis membrane (Spectrapor 5™) is purchased from Fisher Scientific Co. Diethyl ether, ethyl acetate, cyclohexane, and chloroform are purchased from BDH Chemical (Canada). All the other chemicals are of reagent grade, for example, methoxypolyethylene glycol (MW 2000, MW 3350) and stannous-2-ethylhexanoate.

Methods

Preparation of Hemoglobin Solution

Stroma free hemoglobin is prepared according to the standard method (Chang, T. M. S., 1997, "*Blood Substitutes: Principles, methods, products and clinical trial*", vol. I, Karser publisher, Basel). Briefly, hemoglobin is obtained by hypotonic hemolysis of bovine red cells and it is made stroma-free by toluene extraction and is clarified by high speed centrifugation. The resulting solution contained 10 to 15 g hemoglobin/dl. In order to minimize the formation of methemoglobin, the manipulation is carried out at 4° C. and the hemoglobin solution is controlled at pH 7.4.

Preparation of Biodegradable Polymer Nanocapsule Compositions (Standard Method)

Organic Phase:

Dissolve 100 mg (d.l)-polylactic acid (MW 25000) (Polysciences, Warrington, Pa.) in 8 ml acetone. Dissolve 50 mg hydrogenated soybean phosphatidylcholine (Avanti Polar Lipids, Alabaster, Ala.) in 4 ml ethanol with help of Ultrasonic water bath (very low power). Above two solutions were mixed (add either one to another), and use as organic phase.

Aqueous Phase:

Take 0.04 ml of Tween 20, mix with 25 ml 15% (g/dl) hemoglobin.

Preparation:

Slowly inject (8 ml/min.) the organic phase into the aqueous phase under magnetic stirring [with Therm-O-Swirl Stirrer (Precision Scientific Co., Chicago) setting to 6)], under 4° C. The injection head was made with a 0.2 ml pipette tip. The nanocapsules were formed immediately, but, the suspension was keeping stirring for 15 min. The suspension prepared is 37 ml. The organic solvent was partly removed from above suspension prepared by rotary evaporator under vacuum at 20° C. for about 10 minutes. The suspension obtained was 33 ml (i.e. removed 4 ml organic solvent). The remaining suspension was mixed with 15 ml of 0.9% NaCl. Then the organic solvent and free hemoglobin were removed by ultrafiltration (by Amicon ZM 500,000 membrane, MW cut off 500,000). The suspension was repeatedly washed by 0.9% NaCl by ultrafiltration. The operation was carried out at 4° C., with nitrogen.

The nanocapsule compositions prepared according to the standard procedures outlined above were adapted, as described hereinbelow, to provide the nanocapsule compositions of the present invention having improved circulation time and controlled release rates.

As exemplified in accordance with the examples provided hereinbelow, Example II outlines the preparation of nanocapsules having a circulation half-time of 35 hours. In this example, although the nanocapsules themselves circulate for 35 hours T1/2 the contents were found to leak out with a T1/2 of 2 hours or less. Example III exemplifies modifications to the membrane characteristics of Example II which results in nanocapsules that can retain encapsulated agents for longer periods of time. Example IV exemplifies further modifications resulting in improved retention times of encapsulated agents. Example IV combines (1) the methods of modifications of the nanocapsule membrane from Examples II & III with (2) modification to the encapsulated agents themselves e.g. cross-linking macromolecules by different degrees of polymerisation to provide larger molecular weights prior to encapsulation. The details of the modifications are described for each of the examples. Each example from II to IV has a number of different modifications and approaches.

The present invention will be more readily understood by referring to the following examples which are given to illustrate the invention rather than to limit its scope.

EXAMPLE I

Standard Polymeric Nanocapsule Preparations

We first varied the membrane compositions of 5 variations of polymeric nanocapsules and studied their effects on circulation time.

(1) Polylactic acid(PLA)-nanocapsules were prepared by as described above for standard nanocapsules. These PLA-nanocapsules displayed a circulation half-time of about two hours (FIG. 1).

(2) The addition of phospholipids to the polymer membrane of nanocapsules of the standard procedure resulted in only modest increases in circulation time (this item not shown in FIG. 1). In this case, hydrogenated soybean lecithin (HSPC) or distearoyl phosphatidylcholine (DSPC) was incorporated into the PLA nanocapsules.

(3) The incorporation of lipid-polyethylene glycol (PEG) to the polymer membrane of nanocapsules did not result in any significant increases in the circulation time (FIG. 1—PLA-PEG-lipid). Here, 1,2-dietearoyl-glycero-3-phophoethanolamine-N-[poly(ethylene glycol)-2000] was incorporated into the membranes of the PLA nanocapsules.

(4) Adsorption of PEG to the nanocapsules was also performed. 7% PEG (MW 15000) was added to the PLA nanocapsules and left in the suspension for 6 hours. Unfortunately, there were no significant increases in circulation time (FIG. 1—PEG adsorbed to PLA).

(5) Standard PLA-PEG copolymers were prepared by mixing 10 g of methoxypolyethylene glycol (MW 2000) and 10 g of DL-lactic acid and stirred under nitrogen at 160° C. Then 50 μl of stannous 2-ethylhexanoate was added. The mixture was kept at 160° C. for 3 hours. However, this polymer was soluble in water and therefore could not be used in the Hb PLA-nanocapsules process. This composition was deemed unsuitable for use in the encapsulation of water soluble macromolecules within nanocapsules.

EXAMPLE II

Preparation of Hemoglobin Encapsulated Nanocapsule Compositions (1) Organic Phase:
Dissolve 100 mg of the PLA-PEG copolymer prepared as described in details below (Method 2) in 8 ml acetone. Dissolve 50 mg hydrogenated soybean phosphatidylcholine (Avanti Polar Lipids, Alabaster, Ala.) in 4 ml ethanol with the help of Ultrasonic water bath (very low power). Above two solutions were mixed and use as organic phase.

(2) Aqueous Phase:
Take 0.04 ml of Tween 20, mix with 25 ml 15% (g/dl) hemoglobin.

(3) Preparation:
Slowly inject (8 ml/min.)(The injection head is made with a 0.2 ml pipette tips) the organic phase into the aqueous phase under magnetic stirring [with Therm-O-Swirl Stirrer (Precision Scientific Co., Chicago) setting to 6)], at 4° C. The nanocapsules were formed immediately, but, the suspension was keeping stirring for 15 min. The suspension prepared is 37 ml.

The organic solvent was partly removed from above suspension prepared by rotary evaporator under vacuum at 20° C. for about 10 minutes. The suspension obtained was 33 ml (i.e. removed 4 ml organic solvent). The remained suspension was mixed with 15 ml of 0.9% NaCl. Then the organic solvent and free hemoglobin were removed by ultrafiltration (by Amicon ZM 500,000 membrane, MW cut off 500,000). The suspension was repeatedly washed by 0.9% NaCl by ultrafiltration.

The operation was carried out at 4° C., with nitrogen.

It was subsequently determined that a suitable nanocapsule polymer would preferably be soluble in acetone and insoluble in water. The following novel copolymers were investigated for use in preparing nanocapsules of the present invention:

Method 1—One gram of D,L-PLA[M.W. 10,000] and 0.5 g of PEG [M.W. 3350] were dried under vacuums overnight. 5 ml of acetone was added. The mixture was heated to 100° C. for 1 hr under nitrogen. After adding 20 μl of stannous-2-ethylhexanoate, the mixture was heated to 180° C. for another 6 hrs under nitrogen. The final polymer is soluble in acetone. This copolymer was subsequently employed with hemoglobin in the preparation of a biodegradable nanocapsule composition as described above. However, this PLA-PEG copolymer preparation (PEG-PLA method 1) did not increase the circulation half-time sufficiently (FIG. 1).

Method 2—One and a half grams of DL-PLA [M.W. 10,000] and 0.75 g of methoxypolyethylene glycol [M.W. 2000] were dried under vacuums overnight. The mixture was heated to 180° C. for 2 hr under nitrogen. After adding 10 μl of stannous-2-ethylhexanoate, the mixture was heated at 180° C. for another 3 hours under nitrogen. The final polymer is soluble in acetone. This copolymer was subsequently employed with hemoglobin in the preparation of a biodegradable nanocapsule composition as described above. We determined circulation half-times using this preparation (PLA-PEG method 2) in rats and found a circulation half-time of 35 hours (FIG. 1). Thus, this PLA-PEG copolymer preparation was identified as a novel candidate for an improved biodegradable polymeric nanocapsule.

Method 3—Another study was carried out to determine if the use of a higher MW PEG would further increase the circulation time. Two grams of D,L-PLA [M.W. 10,000] and 1 g of PEG [M.W. 3350] were dried under vacuums overnight. 5 ml of acetone was added. The mixture was heated to 100° C. for 1 hr under nitrogen. Then, the mixture was heated to 180° C. for another 10 hours under nitrogen. This copolymer is soluble in acetone. This copolymer was subsequently employed with hemoglobin in the preparation of a biodegradable nanocapsule composition as described above. This preparation did not result in a sufficient increase in circulation half-time (FIG. 1).

EXAMPLE III

Use of PLA-PEG Copolymer as a Nanocapsule Carrier

Once we obtained a nanocapsule with sufficient circulation half-time, we proceeded to study this nanocapsule preparation with the exemplary macromolecule, hemoglobin (Hb). In light of the 35 hour circulation half-time obtained with the PLA-PEG copolymer preparation (Method 2) above, this preparation was further studied as a nanocapsule membrane carrier for the in vivo delivery of hemoglobin. According to the present invention, hemoglobin is employed as an exemplary macromolecule to illustrate the properties of the nanocapsule of the present invention as a carrier for therapeutic agents of interest. However, the present invention is not limited thereto.

Hemoglobin nanocapsules were successfully prepared (as described above).

These nanocapsules displayed circulation half-time of about 35 hours—similar to those nanocapsules prepared without Hb. However, the encapsulated hemoglobin was found to leak out of the nanocapsules after infusion into in vivo circulation and rapidly disappear. The circulation half-time of the Hb component within the nanocapsule carrier was found to be less than 2 hours, while, the nanocapsules themselves continue to circulate with a half-time of 35 hours—even though the membrane is slowly degraded and becomes leaky.

Various steps were employed to solve the problem of leakage of a macromolecule component from the nanocapsules of the present invention, as outlined in Table 1. The hemoglobin nanocapsules were prepared using the detailed method described for PLA-PEG nanocapsules. After this, the resulting hemoglobin nanocapsules were cross-linked using glutaraldehyde. The purpose of this was to cross-link the hemoglobin inside the nanocapsules to provide large macromolecules, e.g. polyhemoglobin. Thus, decreasing the rate of their release from the nanocapsules. In addition, hemoglobin molecules were cross-linked near the internal surface of the nanocapsules so as to decrease the permeability of the membrane of the nanocapsules. Table 1 shows the variations employed to adapt the release rate of the nanocapsule compositions of the present invention, as exemplified together with hemoglobin, including (1) the amount of glutaraldehyde used as shown by cross-linker/hemoglobin ratio; (2) the duration of the cross-linking process as shown by cross-link time; and (3) the concentration of glutaraldehyde used. The circulation half-times of the resulting Hb PLA-PEG nanocapsules are shown in the column under T1/2.

TABLE 1

Procedures used to effect an increase in emoglobin retention time within PLA-PEG-nanocapsules

| PROCEDURE | Crosslinker/Hb (Xlk/Hb) ratio | Crosslink Time (Xlkt) | CrosslinkConc. (Xlkc) | $T_{1/2}$ |
|---|---|---|---|---|
| Hb-nanocapsule before cross-linking 980914 | | | | 1.3 h |
| Hb-nanocapsule 981027 | 8:1 | 2 h | 0.5 M | 4.0 |
| Hb-nanocapsule 990119 | 8:1 | 2 h | 0.5 M | 6.5 |
| Hb-nanocapsule 990126 | 16:1 | 3 h | 0.25 M | 10.0 |
| Hb-nanocapsule 990202C2 | 6:1 | 5 h | 0.25 M | 14.0 |
| Hb-nanocapsule 990302 | 16:1 | 5 h | 0.5 m | 16.0 |
| Hb-nanocapsule 990304 | 16:1 | 20 h | 0.5 M | 12.4 h |

Figure 2:
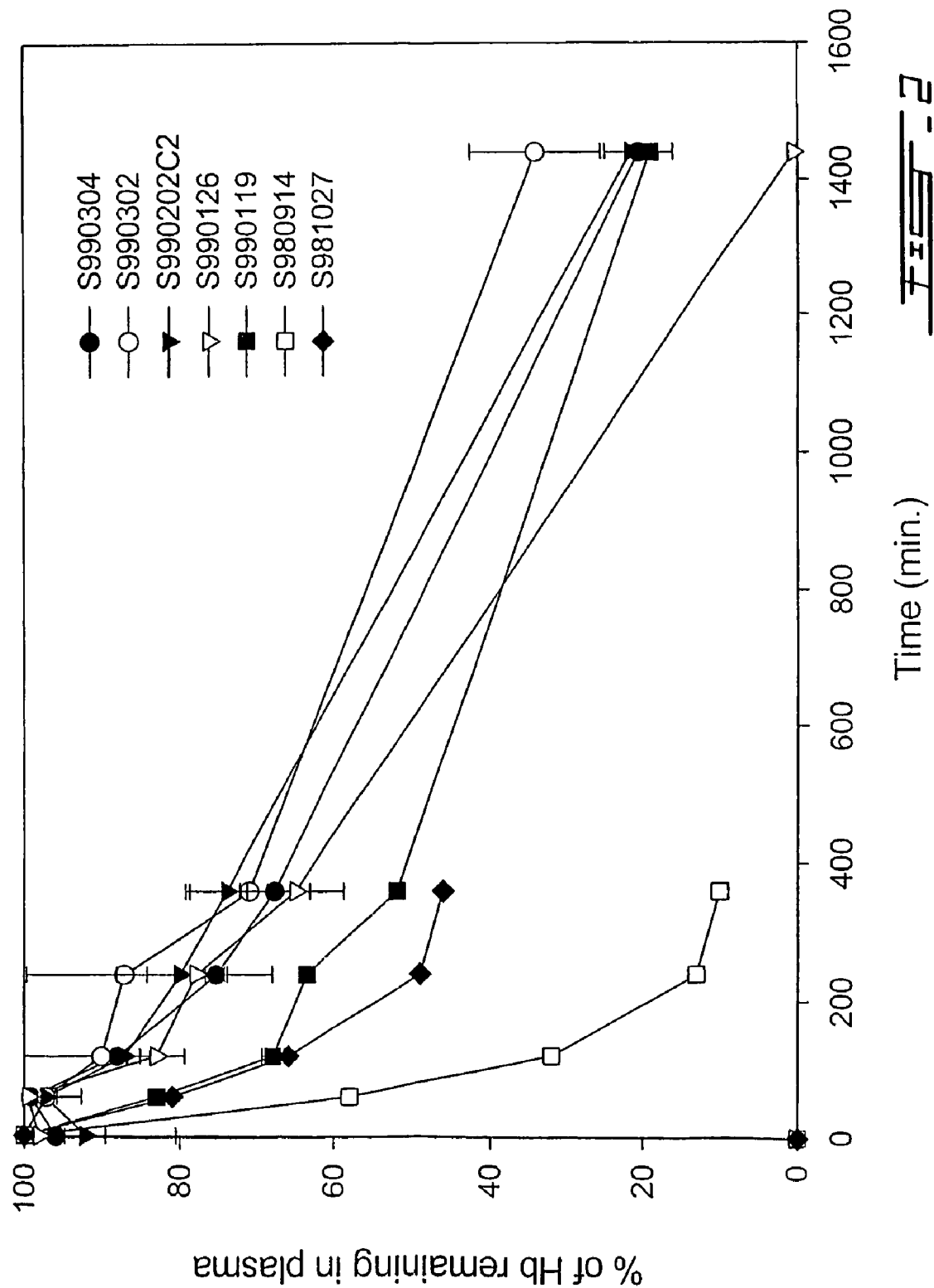
FIG. 2 illustrates a graphical representation of the retention times of Hb in a variety of nanocapsule compositions in accordance with the present invention.

Increasing the cross-linking time to 5 hours with cross-linker concentrations of 0.5M increases the circulation half-time to 16.0 hours (FIG. 2). This is a vast improvement compared to the 2 hours for Hb nanocapsules that have not been cross-linked. This is also higher than the 8 to 12 hours for cross-linked hemoglobin solutions in rats. Furthermore, given that circulation half time is usually much lower in rats than in humans, this result suggests that significant improvement in circulation time can be achieved in human, with the nanocapsule compositions of the present invention. However, we continued to devise novel approaches to decrease even further the release rates of hemoglobin from this nanocapsule composition after infusion.

Cross-Linking Procedures for Hb Nanocapsules

To strengthen the Hb nanocapsule membrane, different approaches including cross-linking were employed. A summary of the different methods studied is shown in Table 2 below and illustrated in FIGS. 3A and 3B.

Table 2 outlines further studies employed in investigating nanocapsule strength, using the above approach of cross-linking the PLA-PEG hemoglobin nanocapsules as shown in Table 1. As presented in Table 2, "Xlink" refers to the ration of glutaraldehyde and hemoglobin as in Table 1; "PLA-PEG" refers to the molecular weight of PLA/PEG used for the preparation of the PLA-PEG hemoglobin nanocapsules; "React" refers to the time (hrs) of cross-linking with the cross-linker; "Separation" refers to the step of concentration of the resulting nanocapsules as detailed in the detailed method for the preparation of PLA-PEG hemoglobin nanocapsules described earlier; "Ethanol" refers to the use of ethanol in the preparation. The first column of Table 2 provides a summary of columns 2 to 6. e.g.

5KX(12:1) 0.25F refers to: PLA with molecular weight of 15 Kd (xlinker ratio of 12:1) reaction time of 0.25 and filtration for separation.

TABLE 2

| METHODS | Xlink | (PLA-PEG) | React (hrs) | Separation | Ethanol |
|---|---|---|---|---|---|
| 5K | | 5000/2000 | | filtration | |
| 5KX(12:1)0.25F | 12:1 | 5000/2000 | 0.25 | filtration | |
| 5KX(8:1)2.5F | 8:1 | 5000/2000 | 2.5 | filtration | |
| 5KX(27:1)0.1F | 27:1 | 5000/2000 | 0.1 | filtration | |
| 5KX(27:1)0.1F-1 | 27:1 | 5000/2000 | 0.1 | filtration | |
| 5KX(36:1)5F | 36:1 | 5000/2000 | 5 | filtration | |
| 5KX(36:1)5F-1 | 36:1 | 5000/2000 | 5 | filtration | |
| 5KX(36:1)5F-2 | 36:1 | 5000/2000 | 5 | filtration | |
| 5KX(16:1)5F | 16:1 | 5000/2000 | 5 | filtration | |
| 5KX(16:1)20F | 16:1 | 5000/2000 | 20 | filtration | |
| 5KX(8:1)5F | 8:1 | 5000/2000 | 5 | filtration | |
| 5KX(8:1)20F | 8:1 | 5000/2000 | 20 | filtration | |
| 5KX(8:1)20F-1 | 8:1 | 5000/2000 | 20 | filtration | |
| 5KX(8:1)20G-2 | 8:1 | 5000/2000 | 20 | Gel-Dialysis | |
| 5KX(8:1)20G | 8:1 | 5000/2000 | 24 | Gel-Dialysis | |
| 5KX(8:1)21GA30 | 8:1 | 5000/2000 | 21 | Gel-Dialysis | 30% |
| 5KX(8:1)20GA25 | 8:1 | 5000/2000 | 20 | Gel-Dialysis | 25% |
| 5KX(8:1)20GA20 | 8:1 | 5000/2000 | 20 | Gel-Dialysis | 20% |
| 15KX(8:1)24G | 8:1 | 15000/2000 | 24 | Gel-Dialysis | |
| 15KX(8:1)48G | 8:1 | 15000/2000 | 48 | Gel-Dialysis | |
| 15KX(8:1)48G-1 | 8:1 | 15000/2000 | 48 | Gel-Dialysis | |
| 15KX(8:1)48G-2 | 8:1 | 15000/2000 | 48 | Gel-Dialysis | |
| 15KPOLYHb | PolyHb | 15000/2000 | PolyHb | Gel-Dialysis | |

Circulation Time of Hb Nanocapsules

Figure 3A:
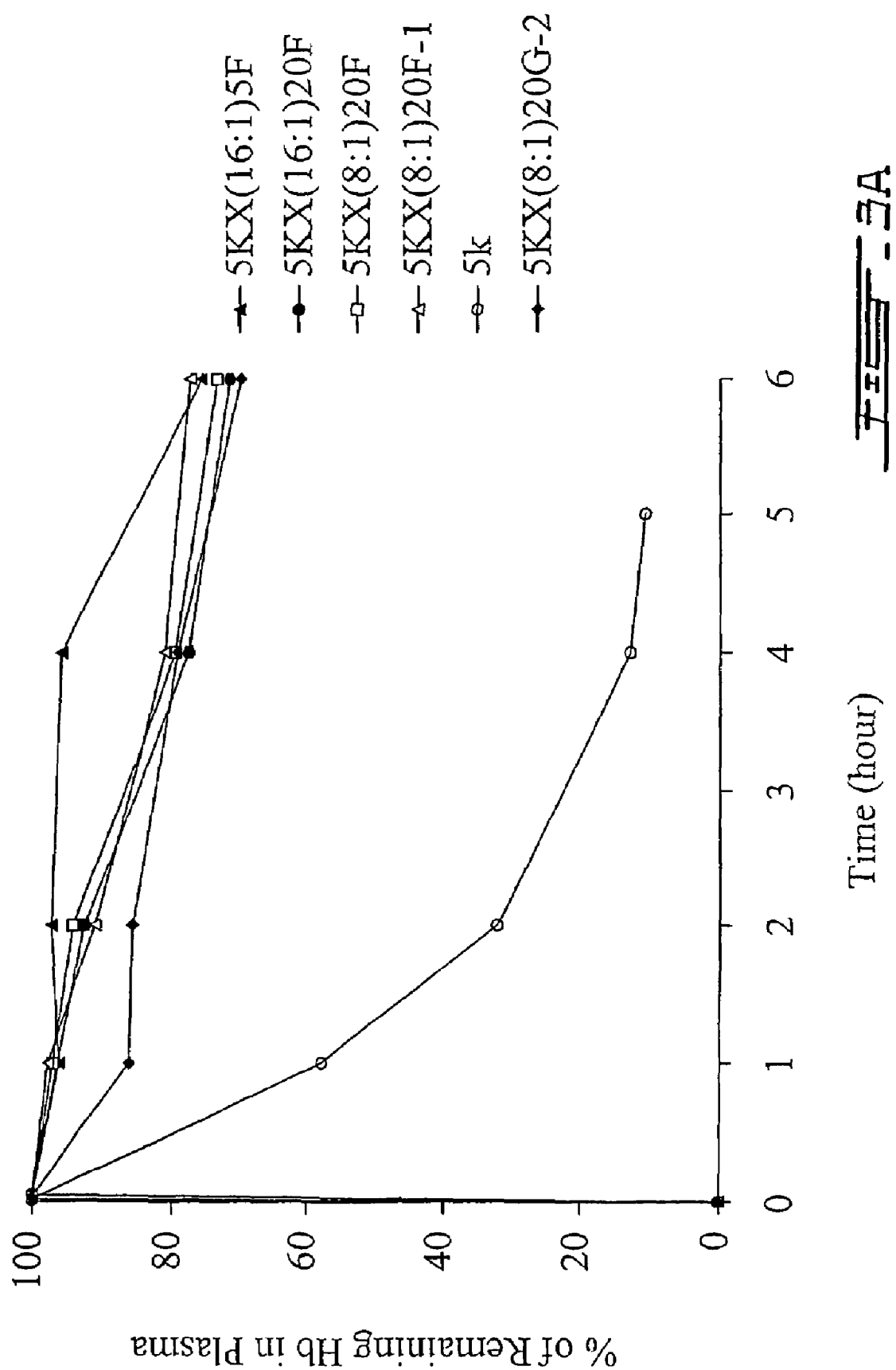

Total blood volume in a 200 gram rat is about 12 ml. 30% top-loading is the infusion of 30% of the total blood volume of a rat with a nanocapsule suspension, i.e. 3.5 ml, into the rat. Results of top-loading of 30% are shown in FIGS. 3A and 3B. FIGS. 3A and 3B illustrate the circulation time obtained from those methods of Table 2 with the best results obtained using PLA of MW of 5K-15K in the nanocapsule composition.

As illustrated in FIGS. 3A and 3B, Hb nanocapsules circulate well in the first 6 hours. However, when samples are taken 24 hours after infusion, they are down to 15-25%. The $T_{1/2}$ of the nanocapsule composition improved from the original (5K) of less than 2 hours to around 14-16 hours.

Biodegradability

Dialysis-gel absorption method was used to separate free Hb or free cross-linked Hb from the PLA-PEG hemoglobin nanocapsules. When Hb nanocapsules samples were obtained 2 hours after infusion and placed in this system, no free Hb was extracted showing that the Hb nanocapsules remained intact. When Hb nanocapsules were incubated with plasma in the dialysis tubing—no Hb was extracted until after 6 hours. After this, free Hb slowly appeared in the suspension and was extracted into the gel, showing that there is slow breakdown in the integrity of the PLA membrane due to biodegradation in plasma starting after 6 hours.

Polymer Composition

In view of the fact that the larger the MW of PLA, the slower is the biodegradability, PLA with a MW of 15-25K was used to form the PEG-PLA copolymer preparation. The use of a higher MW PLA (15K-25K) requires the use of 200° C. for the copolymerisation procedure for PEG-PLA, which may result in the breakdown of the PLA molecule. Size exclusion chromatograph with respect to polystyrene standard, $M_n=6900$, $M_w=8600$, $M_z=7000$, $M_w/M_n=1.24$ shows that the molecular weight of PLA-PEG copolymer was decreased to only 6,900. Thus, substantial breakdown of the PLA molecule was observed.

Figure 4A:
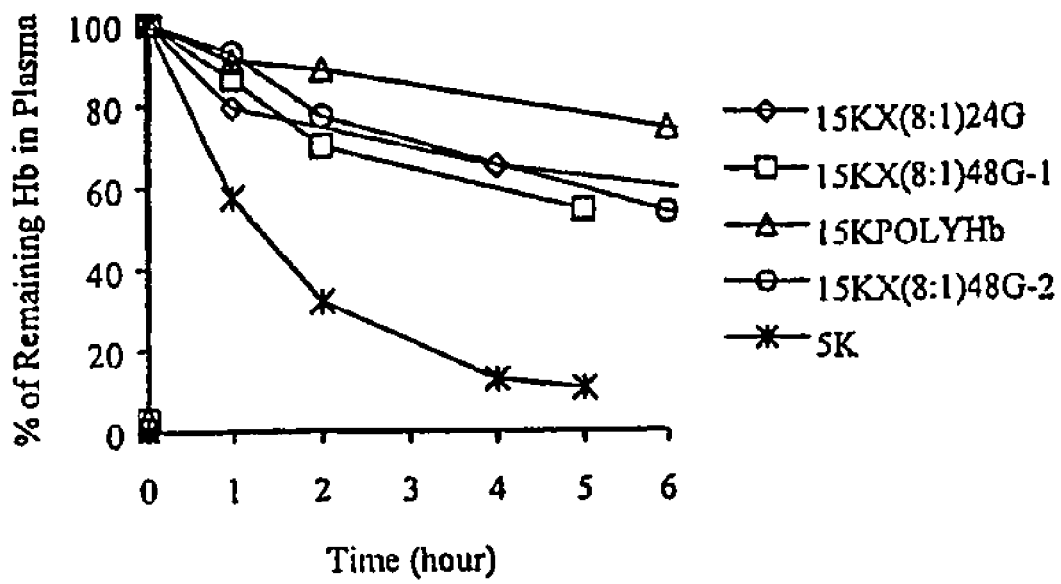
FIG. 4 illustrate the circulation time of a variety of nanocapsule compositions in accordance with the present invention.
Figure 4B:
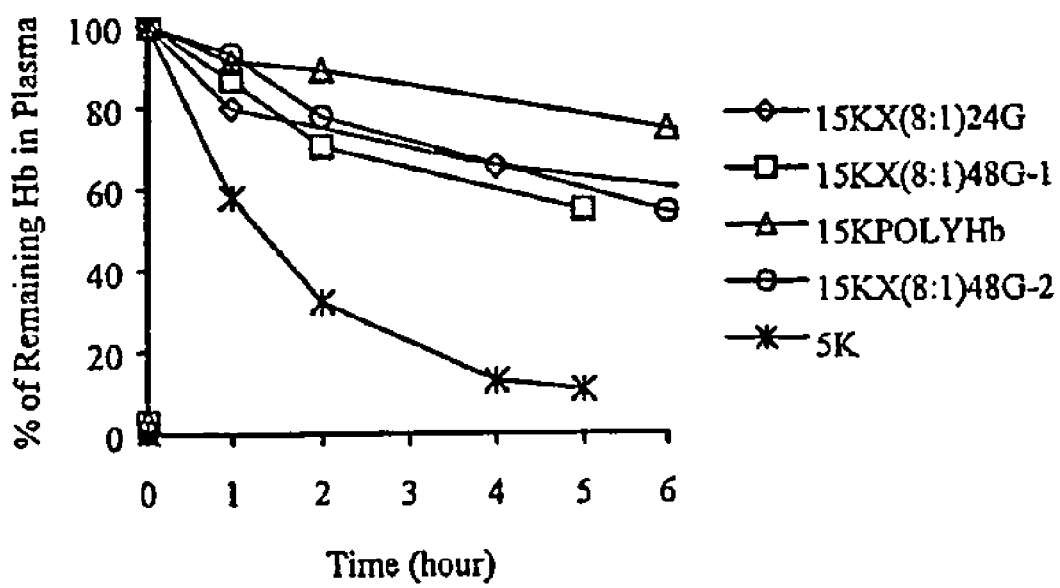

Results obtained with PLA having a MW of 15-25K are exemplified in FIGS. 4A and 4B. No improvement in circulation time was observed, except in the case of 15 POLYHb as discussed hereinbelow.

EXAMPLE IV

Use of PLA-PEG Copolymer Nanocapsule with Polyhemoglobin

Polyhemoglobin is formed by polymerizing hemoglobin molecules to provide macromolecules that are larger in size. Preferably, each polyhemoglobin contains 4-5 hemoglobin molecules chemically linked together.

We have shown that the particle counts of PEG-PLA nanocapsules (both empty and Hb containing) have a circulation half time of 35 hours. However, the circulation $T_{1/2}$ of Hb in the Hb nanocapsules is lower because of the leakage of the enclosed Hb with time. Thus, we have investigated the use of encapsulating polyHb with a MW of about 240K to 360K. This will have less problem of leakage than the smaller native Hb of about MW 64K. As shown in FIGS. 4A & 4B with respect to 15 KPOLYHB, this significantly increased the $T_{1/2}$ from the original 1-2 hours to 14 hours. Accordingly, the present invention provides methods for improving the circulation time of nanocapsule compositions comprising encapsulated agents of therapeutic interest. For example, a macromolecule can be cross-linked to form larger molecules and subsequently be encapsulated by a nanocapsule composition of the present invention. Furthermore, other macromolecules of interest may be mixed with hemoglobin to form a polyhemoglobin complex.

According to the present invention, cross-linking of an agent of therapeutic interest may be performed prior to, or after encapsulation. In addition, encapsulated agents may also be cross-linked to an interior surface of the nanocapsule membrane.

(1) Use of Polyhemoglobin Containing Less Single Hemoglobin Molecules

Variations in membrane composition were investigated to improve the circulation time of the nanocapsules and retention of the hemoglobin inside the nanocapsules during circulation. As a result, efforts focussed on preparations that will maintain a given hemoglobin level to transport oxygen after infusion. This is achieved by improving the Hb nanocapsules according to the methods described above by decreasing the biodegradability of the nanocapsule, altering the permeability of the nanocapsule, such as by cross-linking some of the encapsulated agent to the membrane with a cross-linking agent and/or by using a larger macromolecules for encapsulation. As a result, nanocapsule compositions of the present invention is adapted to provide: (1) a higher initial concentration of an encapsulated agent in vivo and (2) increase the circulation time of the encapsulated agent.

In previous studies, the slope of the disappearing curve of the hemoglobin concentration was analyzed and extrapolated to zero to calculate the circulation half-time. This method is acceptable for comparing and screening a large number of Hb nanocapsules prepared by different formulations. However, this type of analysis is more suitable for looking at the rate of release of drug delivery systems. In accordance with one aspect of the present invention, the actual amount of hemoglobin that is circulating to supply oxygen was investigated. Accordingly, the actual level of hemoglobin remaining in the circulation rather than the slope of the curve was determined.

Using a blood volume in rats of about 60 ml/kg, and knowing the amount of Hb nanocapsules infused, the maximal level of hemoglobin possible after each infusion was calculated. After this the concentration of hemoglobin in the circulation was followed. Circulation half-time in rats for Hb blood substitutes is known to be much shorter than in human. Thus, a baseline reference in comparing the significance of results obtained in rats to human was made. Simultaneous studies using gluataraldehyde PolyHb were conducted. Knowing that the circulation half time of these preparations in human is about 24 hours, we obtained a direct basis for extrapolation to human. However, rats are known to have a much more avid reticulo-endothelial system (RES) for the removal of particulates like nanocapsules. Thus, when extrapolated to human for Hb nanocapsules the circulation half-time would be even higher than what it would actually be in the rats.

(2) Baseline Studies Using Polyhemoglobin

In order to have valid comparisons, all studies in rats used the same protocol. Polyhemoglobin and Hb nanocapsules suspensions were adjusted to have the same hemoglobin concentration of 10 gm/dl. The volume infused was the same for both PolyHb and Hb nanocapsules and is 30% of the total blood volume (30% top-load).

Table 3 shows that 30% top-load using preparations with Hb (10 gm/dl) in rats resulted inpolyhemoglobin (17:1): maximal non-rbc Hb conc. 3.35 gm/dl, falling to half its maximal concentration of 1.67 gm/dl in 14 hrs. From here on, PolyHb (17:1) was used as the basis for comparison to all other preparations including the time for the circulating non-rbc Hb of different preparations to reach 1.67 gm/dl. Thus, in the case of polyhemoglobin (10:1): maximal non-rbc Hb conc is 3.10 gm/dl, falling to 1.67 gm/dl in 10.4 hrs.

30% top-load using EncHb(10:1) resulted in a maximal non-rbc Hb level of only 3.05 gm/dl (S.D.=0.03) (Table 3). This refers to hemoglobin that has been first cross-linked with glutaraldehyde with a crosslinker:hemgolobin ratio of 10:1 and then encapsulated within PLA-PEG nanocapsules. The non-rbc Hb falls to 1.67 gm/dl in 12.3 hours in rats (21 hours in human equivalent).

Calculations based on body weight, blood volume, plasma volume and dilution factors illustrate that the maximum non-rbc hemoglobin concentration for Hb nanocapsules is at least 3.6 gm/dl rather than only 3.05 gm/dl as for EncHb(10:1) in Table 3. This seems to show that a significant part (about 16%) of the infused Hb nanocapsules was removed nearly immediately on infusion. Thus the next step is to try to prevent this.

In the above preparation, hemoglobin was first cross-linked into polyhemoglobin before being encapsulated into the nanocapsules.

The larger molecular size of polyhemoglobin delays the leakage of the hemoglobin as the nanocapsule membrane degrades in the circulation, and therefore increase the circulation half-time (Table 3). We carried out a more detailed analysis of the molecular weight distribution of the polyhemoglobin used in the above preparation based on PolyHb(10:1). We then used a higher degree of polymerization as described in the examples below to improve the degree of polymerization to markedly reduce the amount of single tetrameric hemoglobin (PolyHb 17:1) and encapsulation was performed.

(i) Formulation "EncapHb (17:1)"

The polyhemoglobin "EncapHb (17:1)" was used in the following formulation for hemoglobin nanocapsules. The ratio of the cross-linker (glutaraldehyde) to hemoglobin used in the cross-linking step for forming polyhemoglobin was 17:1 for this formulation. 100 mg of PLA-coPEG and 50 mg phospholipid were dissolved in a mixed solution of ethanol (3 ml) and acetone (6 ml). Then this solution was slowly injected into 25 ml of the above polyhemoglobin solution containing 0.24% Tween 20 under constant magnetic stirring. Diffusion of ethanol and acetone into the aqueous phase resulted in particle formation. The ethanol and acetone in the aqueous phase was easily eliminated by dialysis against saline solution at 4° C.

TABLE 3

| Formula | max Hb | time to 1.67 g/dl (hrs) |
|---|---|---|
| PolyHb (17:1): | 3.35 gm/dl | 14.0 (rats) |
| | | 24 (Human) |
| PolyHb (10:1): | 3.10 gm/dl | 10.4 (rats) |
| | | 17 (Human) |
| EncHb (10:1): | 3.05 gm/dl | 12.3 (rats) |
| | | 21 (Human) |
| EncHb (17:1): | 3.58 gm/dl | 17.1 (rats) |
| | | 29 (Human) |
| EncHb 1.5 (5 k): | 3.60 gm/dl | 20.0 (rats) |
| | | 34 (Human) |
| EncHb 1.0 (5 k)XL | 3.60 gm/dl | 20.3 (rats) |
| | | 35 (Human) |
| EncHb 1.0 (15 k): | 3.57 gm/dl | 21.2 (rats) |
| | | 36 (Human) |
| EncHb 1.5 (15 k): | 3.65 gm/dl | 23.3 (rats) |
| | | 39.9 (Human |
| EncHb 1.5 (15 k)XL | 3.66 gm/dl | 24.2 (rats) |
| | | 41.5 (Human) |

As shown in Table 3, two minutes after infusion, the maximal non-rbc Hb was 3.58 gm/dl(S.D.=0.04). This is significantly higher than the 3.05 gm/dl (S.D.=0.04) for the earlier Hb nanocapsules (EncHb (10:1). This also approaches the maximal possible initial non-rbc Hb concentration. Furthermore, the slope of the disappearance is also much slower, but what is more important is that it took 17.1 hrs (rats) or 29.3 hrs (human) for the non-rbc Hb level to fall to 1.67 gm/dl as compared to 12.3 hrs (rats) or 21.1 hrs (human) for the earlier Hb nanocapsules (EncHb (10:1). This very significant increase was further improved using step-wise incremental formulations until we reached a maximal concentration of 3.66 gm/dl(S.D.=0.03) and 24.2 hrs (rats) or 41.5 hrs (Human) to fall to the level of 1.67 gm/dl (eg. EncHb 1.5 Conc. (5K) to EncHb 1.5 Conc. (15K) XL).

(ii) Formulation "1.5 Conc (5k)"

Figure 5:
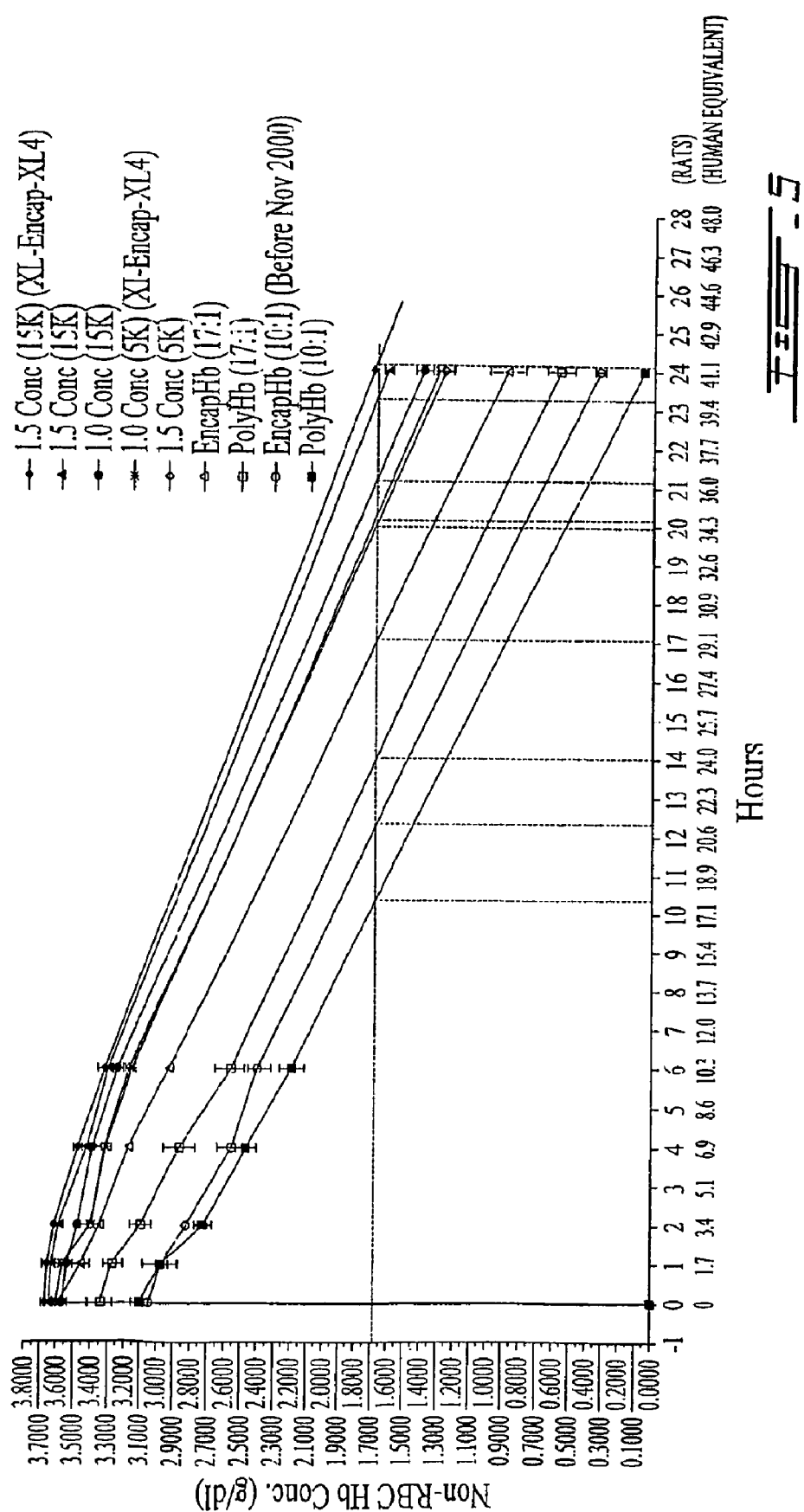
FIG. 5 illustrates a graphical representation of the concentration of non-RBC Hb (g/dl) over time.

A formulation "1.5 Conc (5k)" was prepared in a manner similar to that of "EncapHb (17:1)" formulation above except that the concentration of the PLA-co-PEG was increased to 1.5 in order to have a thicker nanocapsule membrane that would be slower to biodegrade, thereby allowing for a longer circulation time was prepared. As a result, a further increase in circulation time was obtained. Two minutes after infusion, the maximal non-rbc Hb was 3.60 gm/dl(S.D.=0.01) compared to 3.05 gm/dl (S.D.=0.04) for the earlier Hb nanocapsules (Table 3). The slope of the disappearance was also much slower, but what is more important is that it took 20.0 hrs (rats) 34.3 (Human) for the non-rbc Hb level to fall to the level of 1.67 gm/dl (FIG. 5).

(iii) Formulation "2.0 Conc (5k)"

A "2.0 Conc (5k)" formulation was prepared based on the above "1.5 Conc (5k)" formulation except that a higher concentration of polymer was used to further improve the stability of the nanocapsule membrane. However, the Hb nanocapsules formed this way tended to aggregate and therefore were not selected for testing in animal studies.

(iv) Formulation "1.0 Conc (5k)(XL-Ecap, XL4)"

Formulation "EncapHb (17:1)" was modified by adding glutaraldehyde to the Hb nanocapsules suspension after they were formed, to provide a "1.0 Conc (5k)(XL-Ecap, XL4)" Formulation. This formulation cross-linked any surface Hb to further increase the membrane stability. The hemoglobin nanocapsules "encapHb (17:1)" as shown in Table 3 were further treated as follows. The hemoglobin nanocapsules are exposed to a cross-linker, glutaraldehyde by adding this to the suspension. This results in the cross-linking of any Hb near the surface of the nanocapsules so as to further increase the nanocapsule membrane stability. The polymerization of hemoglobin was stopped by adding 2M of lysine (at molar ratio of lysine/hemoglobin=100:1) after 24 hours. This approach also increased the circulation time to the same degree as when using 1.5 concentration of the polymer in Formulation "1.5 Conc (5k)". Thus, two minutes after infusion, the maximal non-rbc Hb was also significantly higher: 3.60 gm/dl (S.D.=0.01) compared to 3.05 gm/dl (S.D.=0.04) for the earlier Hb nanocapsules (Table 3). The slope of the disappearance was also much slower, but what is more important is that it took 20.3 hrs (rats) 34.8 hrs (Human) for the non-rbc Hb level to fall to 1.67 gm/dl (Table 3; FIG. 5).

(v) Formulation "1.0 Conc (15k)"

We also looked at the use of a higher molecular weight PLA to increase the stability of the Hb nanocapsules membrane. For this we replaced the 5K PLA with a 15K PLA for the Formulation "EncapHb (17:1)". As a result, a very significant increase in the circulation half-time of the preparation was observed as compared to that prepared by Formulation "EncapHb (17:1)". Thus, in two minutes after infusion, the maximal non-rbc Hb was: 3.57 gm/dl (S.D.=0.05) compared to 3.05 gm/dl (S.D.=0.04) for the earlier Hb nanocapsules. The slope of the disappearance was also much slower, but what is more important is that it took 21.2 hrs (rat) and 36.3 hrs (human) for the non-rbc Hb level to fall to the level of 1.67 gm/dl (Table 3; FIG. 5).

(vi) Formulation "1.5 Conc (15k)"

We next looked at combining the use of a higher molecular weight PLA (15k) with a higher concentration of the polymer (1.5 times higher). This is done by using the same formulation as Formulation "1.0 Conc. (15k)" above except with a 1.5 concentration of the polymer. This formulation combines (1) using the specially prepared polyhemoglobin with low percentage of single tetrameric hemoglobin; (2) using a 1.5× concentration of the PLA-co-PEG copolymer; and (3) using a higher molecular weight PLA (15k).

This resulted in a further significant increase in the circulation time. In two minutes after infusion, the maximal non-rbc Hb was: 3.6458 gm/dl(S.D.=0.02) compared to 3.05 gm/dl (S.D.=0.04) for the earlier Hb nanocapsules. The slope of the disappearance was also much slower, but what is more important is that it took 23.3 hrs(rats) 39.9 hrs (Human) for the non-rbc Hb level to fall to the level of 1.67 gm/dl (Table 3; FIG. 5).

(vii) Formulation "1.5 Conc (15k)(XL-Ecap, XL4)"

Finally, we combined all the above ways of improving the circulation time by: (1) using the specially prepared polyhemoglobin with low percentage of single tetrameric hemoglobin; (2) using a 1.5× concentration of the PLA-co-PEG copolymer; (3) using a higher molecular weight PLA (15K); and (4) further cross-linking of the Hb nanocapsules with glutaraldehyde.

The circulation time increased slightly from the above when only 3 of the above factors have been incorporated. Thus, in two minutes after infusion, the maximal non-rbc Hb was: 3.6583 gm/dl (S.D.=0.03) compared to 3.05 gm/dl (S.D.=0.04) for the earlier Hb nanocapsules. The slope of the disappearance was also much slower, but what is more important is that it took 24.2 hrs (rats) 41.5 hrs (Human) for the non-rbc Hb level to fall to 1.67 gm/dl (Table 3; FIG. 5).

If we project this to human, a functional circulation time of the most recent Hb nanocapsules (Formulation "1.5 Conc (15k)(XL-Ecap, XL4)") of 41 hours can be expected. This is a very significant and important increase that provides longer function of encapsulated hemoglobin, and thus provides a promising alternative to donor blood. The Hb nanocapsules are likely to have even higher circulation time in human compared to PolyHb. This is because the reticulo-endothelial system (RES) in rats is much more efficient in removing particulates like nanocapsules as compared to PolyHb solution. A further advantage of polyHb is that even if it leaks out after infusion it would continue to act and would not cause any adverse effects. It is fully contemplated that the nanocapsules of the present invention could serve as a useful carrier for other modified Hb including recombinant Hb, as well as other therapeutically effective agents of interest.

EXAMPLE V

Prevention and Conversion of Methemoglobin

With increased hemoglobin in circulation in the body at 37° C., there is a steady increase in the production of methemoglobin. Oxidation of hemoglobin to methemoglobin inside red blood cell is prevented by the enzyme systems of the red blood cells. In the absence of these enzymes, methemoglobin is formed when the circulation time is increased. Accordingly, alternative embodiments of the present invention are provided to prevent the accumulation of methemoglobin when hemoglobin is employed with the nanocapsule compositions disclosed herein.

One embodiment of the present invention includes providing all of the enzymes normally present in the red blood cell together with hemoglobin in the nanocapsule. Another embodiment of the present invention provides a nanocapsule composition that is permeable to external factors such as ascorbic acid, or glutathione which are naturally present in blood that would prevent the accumulation of methemoglobin in vivo. For example, the nanocapsule composition of the present invention can be prepared so that it retains macromolecules like hemoglobin. At the same time, it can be selectively permeable to smaller molecules like ascorbic acid or glutathione.

Currently, hemoglobin encapsulated in nanocapsules of the present invention, is changed slowly to methemoglobin after infusion into the body at 37° C. Methemoglobin, unlike hemoglgobin, can no longer carry and deliver oxygen. If the nanocapsule membrane is made selectively permeable as described above, then while retaining hemoglobin, the membrane would allow ascorbic acid, glutathione or other similar substances from the circulating plasma to diffuse into the nanocapsules. Since these molecules help to prevent hemoglobin from changing to methemoglobin, this enhances the ability of hemoglobin to carry and delivery oxygen.

Hb nanocapsules were prepared to contain all the enzymes of the red blood cells. This was done by using the whole content of red blood cells except the red blood cell membranes (hemolysate) extracted from red blood cells with all the enzymes and hemoglobin. For this we can use any of the procedures described above for the formation of hemoglobin nanocapsules, especially those method that results in prolonged circulation half-time. We prepared Hb nanocapsules with higher methemoglobin level of 7%. We then incubated these nanpcapsules at 37° C. and followed the changes in the % of metHb.

When suspended in Ringer lactate containing 100 mg/dl glucose, metHb increased by 2.5% in 6 hours. Alternativley, when suspended in Ringer lactate containing 100 mg/dl glucose and 0.02 mM NADH, metHb increased in the first hour as above. However, as glucose and NADH entered the nanocapsules to start the multi-enzyme reaction metHb decreased at a rate of 1.5% in 5 hours. This result is very exiting because it shows that we only need to encapsulate fresh red blood cell contents with the normal amount of methemoglobin reductase system. This way, 100 mg glucose (available as blood glucose) and 0.02 mM NADH in the suspending medium not only prevent metHb formation, but also convert metHb back to Hb. By further optimization of the NADH concentration, this can be increased further.

When suspended in Ringer lactate with 100 mg/dl glucose and 0.02 mM NADPH, metHb increased at the same rate as when suspended in Ringer lactate containing 100 mg/dl glucose. This is because unlike NADH, the larger cofactor NADPH is not permeable across the nanocapsules. Since NADPH is not permeable, it can be enclosed inside the nanocapsules. This avoids the need to supply external cofactor and allows the reaction to take place like it does in the RBC. The circulating blood contains close to 100 mg/dl of glucose that can enter the nanocapsules to act with NADPH and the multi-enzyme system. For RBC, blood glucose can enter the RBC by membrane transport.

There are substances in the plasma that prevents methemoglobin formation. Examples include ascorbic acid and glutathione. We suspended Hb nanocapsules of the present invention in solutions, of ascorbic acid, glutathione, or methylene blue. The Hb nanocapsule membrane was permeable to all these factors. As a result, after infusion, the Hb in the nanocapsules were exposed to factors in the circulating plasma that prevent the formation of metHb. In accordance with one embodiment of the present invention, other materials usually present inside red blood cells, including without limitation, enzymes such as catalase, superoxide dismutase and methemoglobin reductase, and cofactors amongst others, may be encapsulated in addition to hemoglobin.

It is fully contemplated that the present invention is adaptable for the preparation of nanocapsule compositions comprising therapeutically effective concentrations of other agents of therapeutic interest, including macromolecules.

Accordingly, the nanocapsule compositions of the present invention may include a variety of agents and/or molecules of therapeutic interest to effect a desired result upon administration to a recipient. Furthermore, the nanocapsule compositions of the present invention may be selectively permeable to agents and/or molecules of therapeutic interest so as to allow the same to permeate the nanocapsule membrane and interact with the encapsulated agent.

According to the present invention there is also provided an effective delivery system for delivering encapsulated agents into in vivo circulation. A delivery system adapted for the step-wise release of an agent of therapeutic interest in vivo is also provided. According to this embodiment, a plurality of nanocapsule compositions each having a predetermined release rate for an encapsulated agent of therapeutic interest may be administered simultaneously to achieve a controlled step-wise release thereof in vivo.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A biodegradable polymeric nanocapsule composition adaptable for use as an artificial red blood cell, said nanocapsule encapsulating an agent of therapeutic interest; wherein said agent of therapeutic interest is cross-linked to the interior surface of the nanocapsule and enhancing in vivo circulation time thereof, said nanocapsule having a bilayer membrane defining an interior surface and an exterior surface and comprising a diblock copolymer consisting of a polylactic acid polymer block and a polyethylene glycol polymer block, wherein said nanocapsule membrane further comprises a lipid component, wherein said diblock copolymer is soluble in acetone and insoluble in water and wherein said polyethylene glycol is present on both the interior surface and the exterior surface of the membrane thereby defining a hydrophilic interior wherein said cross-linked agent of therapeutic interest is present or is entrapped.

2. The nanocapsule membrane composition of claim 1 wherein said lipid component is provided in an amount less than each of said polylactic acid polymer and polyethylene glycol.

3. The nanocapsule membrane composition of claim 1 wherein said polylactic acid polymer has a molecular weight of 5 KDa to 25 KDa.

4. The nanocapsule membrane composition of claim 3 wherein the molecular weight of said polylactic acid polymer is at least 10 KDa.

5. The nanocapsule membrane composition of claim 1 wherein said polyethylene glycol has a molecular weight of at least 2,000 Da.

6. The nanocapsule membrane composition of claim 5 wherein said polyethylene glycol is methoxypolyethylene glycol.

7. The nanocapsule membrane composition of claim 1 having an in vivo circulation halftime of at least 14 hours.

8. The nanocapsule membrane composition of claim 1 wherein said agent of therapeutic interest is a macromolecule.

9. The nanocapsule membrane composition of claim 8 wherein said macromolecule is hemoglobin.

10. The nanocapsule composition of claim 8 wherein said agent of therapeutic interest is a cross-linked macromolecule chain.

11. The nanocapsule membrane composition of claim 1 further adapted to provide a selectively permeable membrane for an encapsulated agent of therapeutic interest.

12. The nanocapsule membrane composition of claim 1 wherein said lipid component is a phospholipid.

13. The nanocapsule membrane composition of claim 1 further adapted to maintain an agent of therapeutic interest in vivo, with a circulation half-time of at least 14 hours.

14. A hemoglobin nanocapsule composition, said composition comprising a biodegradable polymeric nanocapsule membrane encapsulating a therapeutically effective concentration of a hemoglobin preparation; wherein said hemoglobin preparation is cross-linked to the interior surface of the nanocapsule, said nanocapsule membrane comprising a copolymer of polylactic acid polymer and polyethylene glycol; said copolymer being soluble in acetone and insoluble in water; wherein said nanocapsule membrane further comprises a lipid component; wherein said nanocapsule composition is adaptable for enhancing in vivo circulation time of said hemoglobin preparation.

15. The hemoglobin nanocapsule composition of claim 14 wherein said lipid component is a phospholipid.

16. The hemoglobin nanocapsule composition of claim 14 wherein said lipid component is provided in an amount less than each of said polylactic acid polymer and polyethylene glycol.

17. The hemoglobin nanocapsule composition of claim 14 wherein said polyethylene glycol is methoxypolyethylene glycol.

18. The hemoglobin nanocapsule composition of claim 14 wherein said polylactic acid polymer has a molecular weight of 5 KDa to 25 KDa.

19. The hemoglobin nanocapsule composition of claim 18 wherein said hemoglobin is a polymerized hemoglobin.

20. The hemoglobin nanocapsule composition of claim 18, wherein the concentration of the copolymer is increased to provide a nanocapsule membrane having a greater thickness.

21. The hemoglobin nanocapsule composition of claim 17 wherein said polyethylene glycol has a molecular weight of 2,000 Da.

22. The hemoglobin nanocapsule composition of claim 18 wherein the molecular weight of said polylactic acid polymer is 15KDa.

23. The hemoglobin nanocapsule composition of claim 14 further comprising at least one other agent known to inhibit the production of methemoglobin.

24. The hemoglobin nanocapsule composition of claim 14 further adapted to be selectively permeable to molecules present in in vivo circulation; wherein said molecules inhibit the encapsulated hemoglobin from being converted to methemoglobin.

25. The hemoglobin nanocapsule composition of claim 14 wherein said nanocapsule composition is adapted to provide said hemoglobin preparation with an in vivo circulation halftime of at least 14 hours.

26. A method for preparing a nanocapsule membrane composition comprising a polylactic acid and polyethylene glycol diblock copolymer having an enhanced circulation time in vivo, said method comprising: (a) heating a mixture of a polylactic acid polymer and polyethylene glycol (PLA-PEG); (b) adding an aqueous solution comprising an agent of therapeutic interest to said mixture; (c) precipitating a copolymer from said aqueous solution to obtain a nanocapsule composition; (d) cross-linking said agent of therapeutic interest to the interior of the nanocapsule; and (e) extracting the nanocapsule composition therefrom; wherein said composition comprises a biodegradable, polymeric nanocapsule membrane encapsulating said agent of therapeutic interest.

27. The method of claim 26 wherein said copolymer is soluble in acetone and insoluble in water.

28. The method of claim 26 wherein said nanocapsule membrane further includes a lipid component.

29. The method of claim 26 wherein said lipid component is a phospholipid.

30. The method of claim 26 wherein said step of heating is performed in the presence of a catalyst.

31. The method of claim 30 wherein said catalyst is stannous-2-ethylhexanoate.

32. A method according to claim 26 wherein the PLA-PEG mixture includes a PLA component having a molecular weight of at least 10,000.

33. The method of claim 32 wherein the PLA-PEG mixture further includes a PEG component having a molecular weight of at least 2,000 Da.

34. The method of claim 26 wherein said agent of therapeutic interest is a macromolecule.

35. The method of claim 34 wherein said macromolecule is hemoglobin.

36. The method of claim 34 wherein said agent of interest is one of a protein, enzyme, gene, RNA fragment or DNA fragment.

37. The method of claim 26 wherein said polylactic acid polymer has a molecular weight of 5 KDa to 25 KDa.

38. The method of claim 37 wherein said molecular weight is at least 10 KDa.

39. The method of claim 26 wherein said step of heating said copolymer mixture is carried out at at least 180 degrees Celcius.

40. The method of claim 38 wherein said molecular weight is 15 KDa to 25 KDa.

41. The method of claim 40 wherein said step of heating said copolymer mixture is carried out at 200 degrees Celcius.

42. The method of claim 26 wherein the circulation time of the encapsulated agent is also enhanced.

43. A delivery system for enhancing the circulation time of an agent of therapeutic interest in vivo, said system comprising a biodegradable polymeric nanocapsule membrane composition comprising a diblock copolymer membrane encapsulating said agent of therapeutic interest; wherein said agent of therapeutic interest is cross-linked to the interior surface of the nanocapsule; wherein said copolymer membrane includes a copolymer of polylactic acid and polyethylene glycol and is soluble in acetone and insoluble in water; wherein said nanocapsule membrane comprises a lipid component: said copolymer membrane being adaptable to deliver the encapsulated agent of therapeutic interest into in vivo circulation at a controlled rate of release.

44. The delivery system of claim 43 wherein said agent of therapeutic interest is a macromolecule.

45. The delivery system of claim 44 wherein said macromolecule is hemoglobin.

46. The delivery system of claim 43 wherein the biodegradable polymeric nanocapsule composition is further adapted to be selectively permeable to biological components present in in vivo circulation of a recipient.

47. The delivery system of claim 43 wherein said nanocapsule composition is further adapted to encapsulate other biological components together with said agent of therapeutic interest.

48. The delivery system of claim 43 wherein said lipid component is a phospholipid.

49. A delivery system for providing step-wise release of an agent of therapeutic interest in vivo, said system comprising a plurality of biodegradable polymeric nanocapsule compositions each adapted to release an encapsulated agent of therapeutic interest at a different predetermined rate of release in vivo; wherein said encapsulated agent of therapeutic interest is cross-linked to the interior surface of said biodegradable polymeric nanocapsule; wherein each of said plurality of biodegradable polymeric nanocapsules includes a diblock copolymer membrane comprising a copolymer of polylactic acid and polyethylene glycol, said copolymer being soluble in acetone and insoluble in water.

50. The delivery system of claim 49 wherein said agent of therapeutic interest is a macromolecule.

51. The delivery system of claim 50 wherein said macromolecule is hemoglobin.

52. The delivery system of claim 49 wherein said copolymer membrane further includes a lipid component.

53. The delivery system of claim 49 wherein the biodegradable polymeric nanocapsule composition is further adapted to be selectively permeable to biological components present in in vivo circulation of a recipient.

54. The delivery system of claim 49 wherein said nanocapsule composition is further adapted to encapsulate other biological components together with said agent of therapeutic interest.

55. The delivery system of claim 52 wherein said lipid component is a phospholipid.

56. A nanocapsule composition comprising a biodegradable polymeric nanocapsule membrane encapsulating a therapeutically effective concentration of a macromolecule; wherein said macromolecule is cross-linked to the interior surface of the nanocapsule; said nanocapsule membrane comprising a diblock copolymer of polylactic acid polymer and polyethylene glycol; said copolymer being soluble in acetone and insoluble in water; wherein said nanocapsule membrane comprises a lipid component; wherein said nanocapsule composition is adaptable for enhancing the in vivo circulation time of said macromolecule.

57. The nanocapsule composition of claim 56 wherein said lipid component is provided in an amount less than each of said polylactic acid polymer and polyethylene glycol.

58. The nanocapsule composition of claim 56 wherein said polyethylene glycol is methoxypolyethylene glycol.

59. The nanocapsule composition of claim 56 wherein said polylactic acid polymer has a molecular weight of 5 KDa to 25 KDa.

60. The nanocapsule composition of claim 59 wherein the a concentration of the copolymer is increased to provide a nanocapsule membrane having a greater thickness.

61. The nanocapsule composition of claim 58 wherein said polyethylene glycol has a molecular weight of 2,000 Da 62. The nanocapsule composition of claim 59 wherein the molecular weight of said polylactic acid polymer is 15 KDa.

63. The nanocapsule composition of claim 56 further adapted to be selectively permeable to molecules present in in vivo circulation.

64. The nanocapsule composition of claim 56 wherein said nanocapsule composition is adapted to maintain said macromolecule with an in vivo circulation half-time of at least 14 hours.

* * * * *

UNITED STATES PATENT AND TRADEMARK OFFICE
CERTIFICATE OF CORRECTION

PATENT NO. : 7,498,045 B2 Page 1 of 1
APPLICATION NO. : 10/488116
DATED : March 3, 2009
INVENTOR(S) : Thomas M. S. Chang et al.

It is certified that error appears in the above-identified patent and that said Letters Patent is hereby corrected as shown below:

Title page item [73] Assignee should read as follows: McGill University

Signed and Sealed this

Third Day of November, 2009

David J. Kappos
*Director of the United States Patent and Trademark Office*